United States Patent [19]

Yasue

[11] Patent Number: 5,443,958
[45] Date of Patent: Aug. 22, 1995

[54] 2-ACRYLAMINE-2-METHYL-1-PROPANE-SULFONIC ACID ENHANCEMENT OF ALKALINE PHOSPHATASE LABEL DETECTION

[75] Inventor: Hiroshi Yasue, Sakura, Japan

[73] Assignee: Director-General, National Institute of Animal Industry, Ibaragi, Japan

[21] Appl. No.: 895,172

[22] Filed: Jun. 5, 1992

Related U.S. Application Data

[63] Continuation-in-part of Ser. No. 230,338, Aug. 9, 1988, abandoned.

[30] Foreign Application Priority Data

Aug. 14, 1987 [JP] Japan .................. 62-203292

[51] Int. Cl.⁶ ........................................ G01N 33/53
[52] U.S. Cl. ............................ 435/7.9; 435/5;
  435/6; 435/7.4; 435/7.5; 435/7.92; 435/7.93;
  435/7.94; 435/7.95; 435/21
[58] Field of Search .............. 435/5, 6, 7.4, 7.5,
  435/7.9, 7.92–7.95, 21; 562/105

[56] References Cited

U.S. PATENT DOCUMENTS

| | | | |
|---|---|---|---|
| 4,472,499 | 9/1984 | McCroskey | 435/4 |
| 4,555,484 | 11/1985 | LaRossa et al. | 435/21 |
| 4,748,115 | 5/1988 | Steaffens | 435/21 |
| 4,782,016 | 11/1988 | Norton | 435/7 |
| 4,784,948 | 11/1988 | Scott | 435/69.3 |

FOREIGN PATENT DOCUMENTS 0122028 10/1984 European Pat. Off. .............. 435/4

OTHER PUBLICATIONS

Yasue et al, "Enhancement of the Sensitivity for In Situ Detection of Alkaline Phosphatase using a Homopolymer of 2-Acrylamide 2-Methylpropane Sulfonate", Arohybical Biochemistry 169 (1988) pp. 410–414.

Yasue et al, Analytical Biochemistry, vol. 169 (1988) pp. 410–414.

Dao, Journal of Immunological Methods, vol. 82 (1985) pp. 225–231.

Blake et al, Analytical Biochemistry, vol. 136 (1984) pp. 175–179.

Holt, "A New Approach to the Cytochemical Localization of Enzymes" Proc. R. Soc. B 142 (1954) pp. 160–169.

DeJong et al, "Sensitivity of Various Visualization Methods for Peroxidase and Alkaline Phosphatase Activity in Immundenzyme Histochemistry," 1985 Histochemical Journal pp. 1119–1130.

Towbin et al, "Electrophoretic Transfer of Proteins from Polyacrylamide gels to Nitrocellulose Sheets: Procedure and Some Applications", Procs Natl Acad Sci USA, 1979 pp. 4350–4354.

Dzo, "An Improved Method of Antigen Detection on Nitrocellulose: In Situ Alkaline Phosphatase Congugated Antibody", Journal of Immunological Methods, B2 (1985), pp. 225–231.

Blake et al, "A Rapid Sensitive Method for Detection of Alkaline Phosphatase Conjugated Anti–Antibody on Western Blots," Analytical Biochemistry 136 (1984) pp. 175–179.

March et al, "A Simplified Method for Cyanogen Bromide Activation of Agarose for Affinity Chromotography," Analytical Biochemistry 60 (1974) pp. 149–152.

McGadey, "Tetrazolium Method for Nonspecific Alkaline Phosphatase," Histochemie 23 (1970), pp. 180–184.

CRC Handbood Immunoblotting of Proteins, vol. I Technical Descriptions, pp. 27, 182 184 (CRC Press 1988).

*Primary Examiner*—Carol A. Spiegel
*Attorney, Agent, or Firm*—Nikaido, Marmelstein, Murray & Oram

[57] ABSTRACT

A first solution containing Tris-HCl, $MgCl_2$, a homopolymer of 2-acrylamide-2-methylpropanesulfonate (AMPS) and agarose is applied to a filter having alkaline phosphatase to be detected. A second solution containing Tris-HCl, $MgCl_2$, homopolymer of AMPS, 5-bromo-4-chloroindoxyl phosphate, nitroblue tetrazolium and agarose is applied onto a film formed by the first solution.

5 Claims, No Drawings

2-ACRYLAMINE-2-METHYL-1-PROPANESULFONIC ACID ENHANCEMENT OF ALKALINE PHOSPHATASE LABEL DETECTION

This is a continuation-in-part application of my patent application Ser. No. 07/230,338 filed Aug. 9, 1988, now abandoned.

BACKGROUND OF THE INVENTION

This invention relates to a method for detecting alkaline phosphatase used in the field of biological and medical studies, particularly employed in the field of clinical tests.

Various methods for detecting alkaline phosphatase in situ have been already known, for example methods using naphthol AS phosphoric acid, nAS-MX phosphoric acid, indoxyl phosphoric acid, employing both of indoxyl phosphoric acid and tetrazolium compound, and other methods.

However, from the viewpoint of the sensitivity of the detection and the stability of stored samples, the method employing both the indoxyl phosphoric acid and tetrazolium compound is currently used for this purpose of detection.

SUMMARY OF THE INVENTION

The object of the present invention is to provide a method which may improve the detection-sensitivity to alkaline phosphatase.

According to the present invention, there is provided a method for detecting alkaline phosphatase consisting of the steps of:
  providing a first solution containing 10 mM of Tris-HCl (pH 9.0), 5 mM of MgCl$_2$, a homopolymer of 0.1%. 2-acrylamide-2-methylpropanesulfonate (AMPS);
  providing a second solution containing 10 mM of Trls-HCl (pH 9.0), 5 mM of MgCl$_2$, homopolymer of 0.01% AMPS, 200 μg/ml of 5-bromo-4-chloroindoxyl phosphate, and 300 μg/ml of nitroblue tetrazolium; and
  applying the first and second solution to a target material to detect alkaline phosphatase.

In accordance with the present invention, the detection-sensitivity to alkaline phosphatase can be remarkably enhanced by the addition of 2-acrylamide-2-methylpropanesulfonate.

EXAMPLE

A standard alkaline phosphatase was applied to a nitrocellulose filter as dot and immobilized thereon. A first reaction solution consisting of 10 mM of Tris-HCl (pH 9.0), 5 mM of MgCl$_2$, a homopolymer of 0.1% 2-acrylamide-2-methylpropanesulfonate (AMPS) and a 0.7% agarose was applied to the nitrocellulose filter to form a thin film the avidin-alkaline phosphatase, and the agarose is solidified.

Then a second reaction solution containing 10 mM of Tris-HCl (pH 9.0), 5 mM of MgCl$_2$, homopolymer of 0.01% AMPS, 200 μg/ml of 5-bromo-4-chloroindoxyl phosphate (BCIP), 300 μg/ml of nitroblue tetrazolium (NBT). The BCIP and NBT had the same amount as that of the conventionally used reactive liquid, and 0.7% agarose was layered on the solidified film of the first reaction solution. The layered film thus prepared was used for detection of a target alkaline phosphatase. The color of the filter changes with the target alkaline phosphatase and the changed color is compared with the color of the standard alkaline phosphatase to detect the target alkaline phosphatase.

In the reaction system, it was assumed that (i) the poly-AMPS ionically held NBT molecules but not BCIP so that only the BCIP penetrated the active center of the enzyme (avidin-alkaline phosphatase) through agarose, and (ii) the. indoxyl molecules released from the enzyme by the dephosphoration of BCIP were reacted with the NBT molecules in the vicinity of the enzyme to form the insoluble reaction product. Thus, the activity of the enzyme is maintained, which provides enhancement of detection-sensitivity to a target enzyme.

In order to test the validity of the assumption in the above reaction system, the following experiments were performed. The above described filter was incubated at 37° C. for 24h in a sealed nylon bag.

As controls, (i) a solution containing 10 mM Tris-HCl (pH 9.0), 5 mM MgCl$_2$, 200 μg/ml BCIP, 300 μg/ml NBT, and 0.7% agarose (referred to as control RM) was spread on a nitrocellulose filter to form a solid plate 2-3 mm thick, and (ii) the nitrocellulose filter was immnersed in a reaction mixture containing 100 mM Tris-HCl (pH 9.5), 100 mM NaCl and 5 mM MgC12, 200 μg/ml BCIP and 300 μg/ml NBT. The control was processed as described above. The reactions were terminated by immersing the sample in 20 mM Tris-HCl (pH 8.0), 10 mM EDTA. A part of the nitrocellulose filters was peeled off from agarose in order to examine the deposition state of the reaction product. The reaction product was observed in the agarose as well as on the nitrocellulose filter developed in the present invention, whereas it was observed on the nitrocellulose-filter but little in the agarose in the controls. These results indicated that the reactions postulated earlier took place in the system of the present invention.

It has been found that the method of the present invention has a detection-sensitivity of about 3 times that of the conventional method.

As described above, according to the method of the present invention, when alkaline phosphatase is detected by employing a reactive solution composed of indoxyl phosphoric acid and. tetrazolium compounds, a high molecular weight substance containing a strongly acidic group as its side chain is added to the above-mentioned solution, thereby effecting advantages of reduction of the required quantity for the specimen and enhancement of the precision level of the analysis in the fields of clinical tests or related studies.

While the presently preferred embodiment of the present invention has been described, it is to be understood that various changes and modifications may be made without departing from scope of the invention as set forth in the appended claims.

What is claimed is:

1. A method for determining an amount of an analyte in a test sample, comprising:
  contacting the test sample with a membrane to which said analyte specifically binds via a specific binding reaction;
  then contacting said membrane with a binder labeled with alkaline phosphatase, whereby said binder specifically binds to analyte specifically bound to said membrane via a specific binding reaction;

then contacting said membrane with a first solution comprising 0.7% agarose, Tris-HCl, MgCl$_2$ and 2-acrylamide-2-methylpropane sulfonate homopolymer;

then allowing said first solution to solidify to form a first film layer;

then contacting said membrane with a second solution comprising 0.7% agarose, Tris-HCl, MgCl, 2-acrylamide-2methylpropane sulfonate homopolymer, 5-bromo-4-chloroindoxyl phosphate and nitro blue tetrazolium;

then allowing said second solution to solidify to form a second film layer; and then determining the amount of said alkaline phosphatase bound to said membrane as an indication of the amount of said analyte in said test sample.

2. The method as recited in claim 1, wherein said first composition comprises 0.7% agarose, 10mM pH 9.0 Tris-HCl, 5mM MgCl$_2$, and 0.1% 2-acrylamide-2-methylpropane sulfonate homopolymer.

3. The method as recited in claim 1, wherein said second composition comprises 0.7% agarose, 10mM pH 9.0 Tris-HCl, 5 mM MgCl$_2$, 0.01% 2-acrylamide-2-methylpropane sulfonate homopolymer, 5-bromo-4-chloroindoxyl phosphate and nitro blue tetrazolium 4. The method as recited in claim 1, wherein said first solution comprises 0.7% agarose, 10mM pH 9.0 Tris-HCl, 5 mM MgCl$_2$, and 0.1% 2-acrylamide-2methylpropane sulfonate homopolymer;

said second solution comprises 0.7% agarose, 10mM Ph 9.0 Tris-HCl, 5 mM MgCl2, 0.01% 2-acrylamide-2-methylpropane sulfonate homopolymer, 5-bromo-4-chloroindoxyl phosphate and nitro blue tetrazolium; whereby said alkaline phosphatase reacts with said 5-bromo-4chloroindoxyl phosphate and nitro blue tetrazolium to produce a precipitate of insoluble chromogen, and the amount of said precipitate of insoluble chromogen is measured to determine said amount of said alkaline phosphatase bound to said membrane.

5. In a membrane-based specific binding assay for determining an amount of an analyte in a test sample comprising immobilizing any of said analyte in the sample on said membrane, and then contacting said membrane with a binder labeled with alkaline phosphatase, whereby said binder specifically binds to said analyte bound to said membrane, the improvement comprising:

subsequently contacting said membrane with a first solution comprising 0.7% agarose, Tris-HCl, MgCl$_2$ and 2-acrylamide-2-methylpropane sulfonate homopolymer;

then allowing said first solution to solidify to form a first film layer;

then contacting said membrane with a second solution comprising 0.7% agarose, Tris-HCl, MgCl$_2$, 2-acrylamide-2-methylpropane sulfonate homopolymer, 5-bromo-4-chloroindoxyl phosphate and nitro blue tetrazolium;

then allowing said second solution to solidify to form a second film layer; and then determining the amount of said alkaline phosphatase bound to said membrane as an indication of the amount of said analyte in said test sample.

* * * * *